United States Patent [19]
Brenman et al.

[11] Patent Number: 5,117,840
[45] Date of Patent: Jun. 2, 1992

[54] ANAL SPHINCTER TRAINING DEVICE

[75] Inventors: Henry S. Brenman, Cinnaminson, N.J.; Donald R. Taylor, Jr., Philadelphia, Pa.

[73] Assignee: Biosonics, Mt. Laurel, N.J.

[21] Appl. No.: 352,691

[22] Filed: May 5, 1989

Related U.S. Application Data

[63] Continuation of Ser. No. 938,560, Dec. 5, 1986, abandoned.

[51] Int. Cl.⁵ .............................. A61N 1/36; A61N 1/04
[52] U.S. Cl. ..................................... 128/788; 128/421
[58] Field of Search ............... 128/788, 419 E, 419 S, 128/421, 422, 423 R, 642

[56] References Cited

U.S. PATENT DOCUMENTS

| | | | |
|---|---|---|---|
| 2,808,834 | 10/1957 | Marden | 128/419 S |
| 3,403,684 | 10/1968 | Stiebel et al. | |
| 3,516,413 | 6/1970 | McDonald et al. | 128/422 |
| 3,749,100 | 7/1973 | Von Der Mosel | |
| 3,800,800 | 4/1974 | Garbe et al. | 128/788 |
| 3,933,147 | 1/1976 | DuVall et al. | |
| 4,106,511 | 8/1978 | Erlandsson | |
| 4,124,028 | 11/1978 | Gallo | 128/422 X |
| 4,153,059 | 5/1979 | Fravel et al. | 128/422 |
| 4,349,031 | 9/1982 | Perlin | 128/642 |
| 4,520,825 | 6/1985 | Thompson et al. | 128/422 |

FOREIGN PATENT DOCUMENTS

| | | | |
|---|---|---|---|
| 2261737 | 9/1975 | France | 128/788 |
| 206545 | 11/1939 | Switzerland | |

OTHER PUBLICATIONS

Schaudinischky Med. & Biol. Engng., vol. 7, pp. 341-343 (1969).
Wright et al., Brit J Surg, pp. 38-41 (1985).
Janneck Proq. Pediatr. Surg. pp. 119-139 (1976).
Hopkinson et al. The Lancet, pp. 297-298 (1960).
Glen J. Pediatr. Surg., pp. 138-142 (1971).
Collins et al. Scand. J. Gastroenterol, pp. 395-400 (1968).

Primary Examiner—Lee S. Cohen
Attorney, Agent, or Firm—Reed Smith Shaw & McClay

[57] ABSTRACT

An apparatus is provided for restoring fecal continence to a patient. The apparatus comprises an electrical stimulation probe for insertion into the anus of a patient and associated electronics for producing a pulsatile waveform electrical output adapted for optimal physiological stimulation.

9 Claims, 8 Drawing Sheets

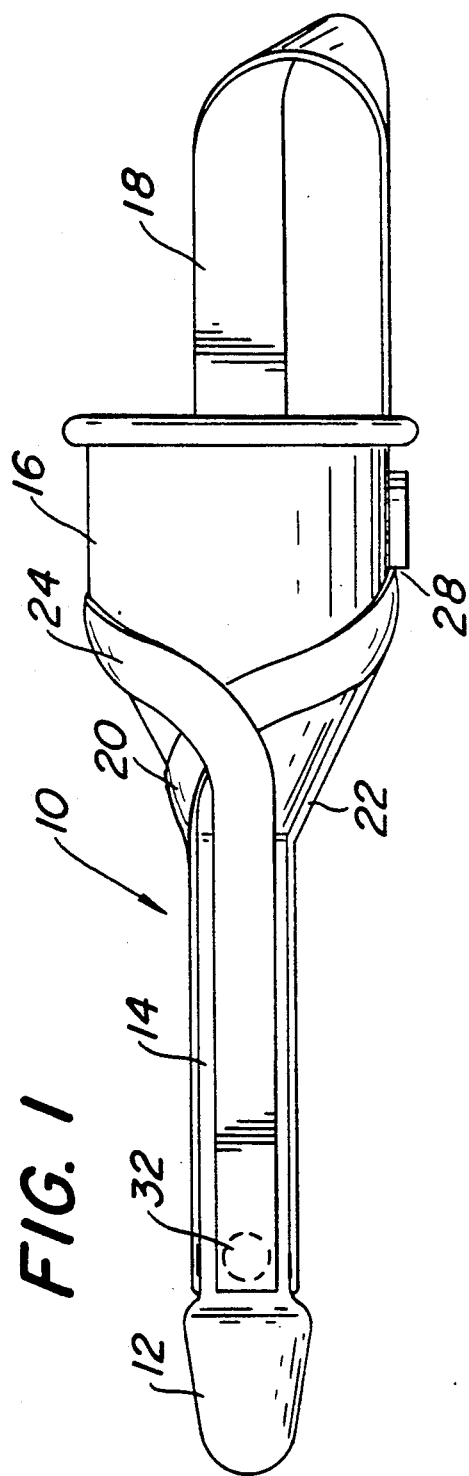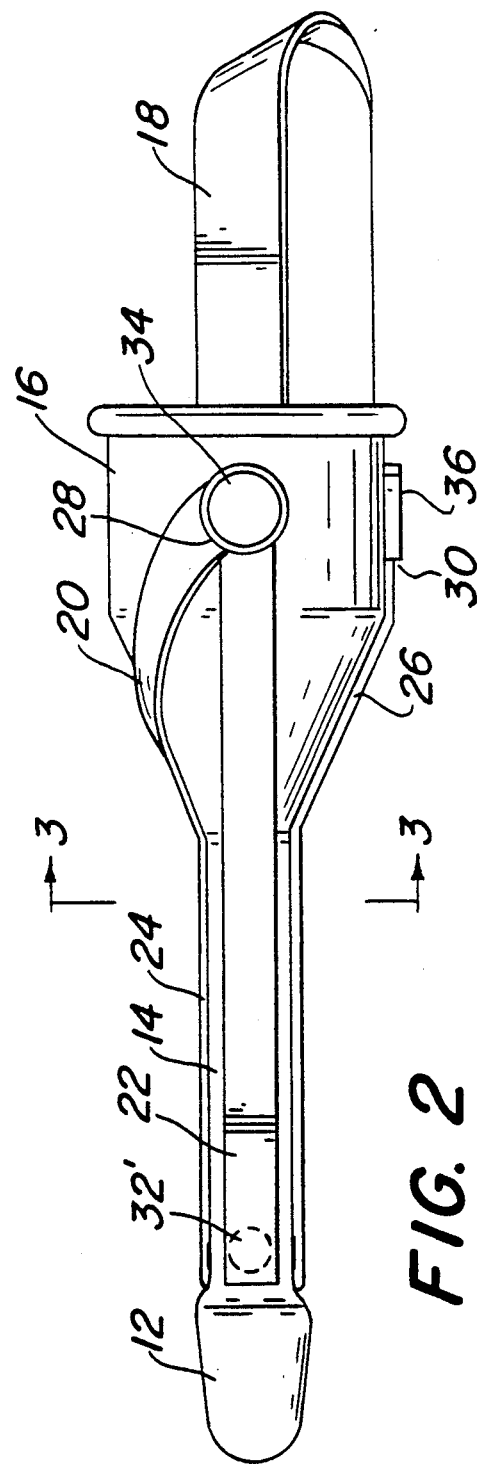

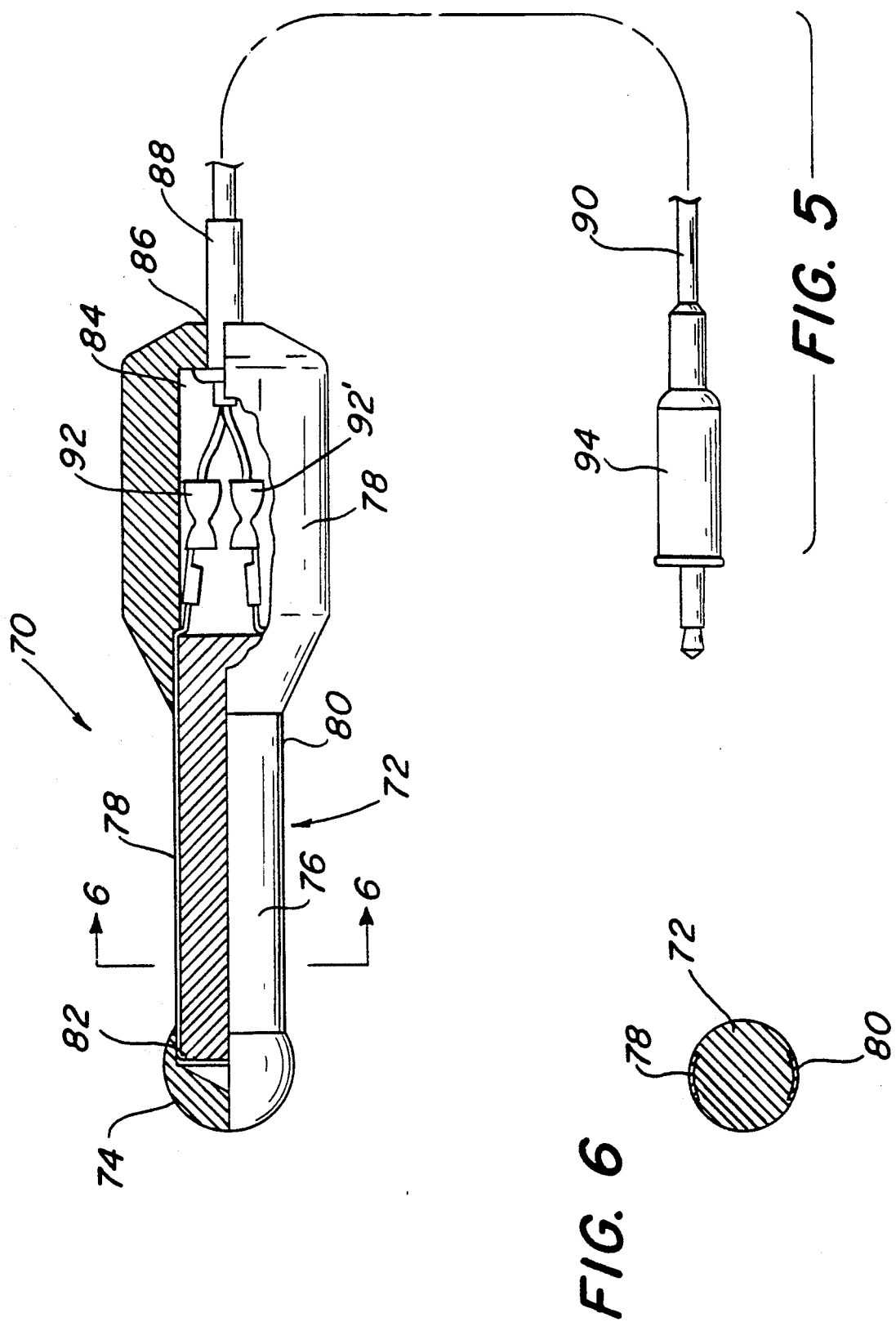

ANAL SPHINCTER TRAINING DEVICE

BACKGROUND OF THE INVENTION

Anal Incontinence is a problem which affects an estimated one million people in the United States today. Defined as the failure of voluntary control of the external anal sphincter, anal incontinence is a frequent and major problem in elderly individuals, yet is not limited to a specific population based on age. Incontinence is often a deleterious side effect of colonic and sphincter surgery; i.e., hemorrhoidal, colectomy and ulcerative colitis ideal pouch reconstruction, which sometimes results in the loss of control of the external sphincter muscle. When individuals become incontinent, the quality of their lives is decreased due to their inability to control normal bowel functions.

According to Gray's Anatomy (Gray, *Anatomy of the Human Body*, 1966), the two sphincter muscles of the anal region are the sphincter ani externus and the sphincter ani internus.

The sphincter ani externus, sometimes referred to as the external sphincter muscle, is composed of striated muscle fibers. The external anal sphincter is a cylinder of skeletal muscle supplied by the somatic nervous system and subject to voluntary control. The deeper portion of the muscle completely surrounds the anal canal. The superficial layer constitutes the major portion of the muscle, surrounding the end of the anal canal and encircling the anus. This muscle is always in a state of tonic contraction and, having no antagonistic muscle, keeps the anal canal and orifice closed.

The sphincter ani internus, or internal sphincter muscle, is composed of circular smooth muscle and is supplied by the autonomic nervous system, rendering it beyond voluntary control. The internal sphincter muscle is incapable of closing the anal canal and orifice.

Defecation in normal individuals is the result of reactions to local stimuli known as "defecation reflexes," and the relaxation of the external sphincter muscle. When fecal material enters the rectum causing distension of the rectal wall, the reflexes responsible for defecation are initiated. The fecal material is forced toward the anus by peristalitic waves in the descending colon, sigmoid, and rectum, accompanied by a decrease in the tonic constriction of the internal sphincter muscle. The movement of feces towards the anus usually results in an instantaneous contraction of the external sphincter muscle which temporarily prevents defecation. When the contraction of the external sphincter muscle is maintained, the peristaltic waves decrease as the rectum adapts to its new volume of material. The reflex waves will not usually return until an additional amount of feces has entered the rectum. However, when sufficient fecal material is already present in the rectum, voluntary contraction of the external sphincter muscle will not stop the increasing frequency of the peristaltic waves. These waves will continue until the fecal material has been eliminated, decreasing the distension of the rectal walls, and thus the defecation reflexes The major difference in the defecation process between normal and incontinent individuals is the degree of control an individual has over his external sphincter muscle. Incontinence usually results from either an inability to voluntarily control the external sphincter muscle, or complete dysfunction of the muscle itself. The largest population suffering from anal incontinence is the aged, afflicted with generalized neurological disorders. A significant percentage of these individuals have normally functioning anal sphincter muscles, but become incontinent due to deficient cortical awareness of rectal filling.

Complete flaccidity and dysfunction of the external sphincter muscle will also result in anal incontinence. This can occur when the nerve impulses from the spinal cord are blocked. These impulses control the tone or residual degree of contraction in a skeletal muscle, such as the external sphincter. The severing of nerve impulses to the muscle reduces the skeletal muscle tone and ultimately leads to uncontrolled defecation.

In a high percentage of the cases, the inability of the individual to control the external sphincter muscle, due to either a neurological disorder or muscle dysfunction, will result in anal incontinence.

Electrical stimulation of normal skeletal muscles elicits a contraction response. Should the nerve impulses to a skeletal muscle be blocked, the individual cannot voluntarily control the muscle. However, the skeletal muscle will still respond to electrostimulation even though there is no physical connection between the muscle and the nerve impulses. This was successfully demonstrated in normal individuals by Wright et al., dealing with a specific skeletal muscle, the external anal sphincter. [Brit. J. Surg., pp. 38-41 (1985)] Subjects were injected with a spinal anesthetic agent designed to block the nerve impulses controlling the external sphincter muscle. Following the administering of the anesthetic agent, the subject showed no spontaneous electromyographic activity, indicating that the nerve impulses to the external sphincter had been completely blocked. Direct electrical stimulation was then applied to the external sphincter muscle producing a contraction of the muscle.

Similar work was performed by Collins, Brown, and Duthie again using continent subjects, blocking the neuromuscular junction with an anesthetic agent. [Scand. J. Gastroenterol., pp. 395-400 (1968)] When the electrical stimulation was applied, the external anal sphincter muscle contracted, closing the anal canal and the anus. Electrical stimulation caused the voluntary muscle to contract.

The work of C. Janneck with incontinent patients using direct electrical stimulation of the external sphincter muscle indicates that neurogenic anal incontinence can be successfully treated by direct stimulation of the anus. [Prog.-Pediatr.-Surg., pp. 119-139 (1976)] In the four subjects treated, anal continence was obtained in all cases following a course of daily treatment, lasting for approximately three months.

An intra-anal electrode was described by Hopkinson and Lightwood in 1966. [The Lancet, pp. 297-298 (1960)] Their research was a continuation of the work performed by Caldwell in 1963, who reported that direct electrical stimulation of the external sphincter muscle could be used to control anal incontinence. Hopkinson and Lightwood further demonstrated that the tone of the external sphincter muscle could be increased using continuous electrical stimulation administered via a rectally inserted plug. Based on their clinical research, the use of an energized anal plug was effective in providing anal continence. Rapid progress was made in improving the tone of the external sphincter muscle in cases where the muscle had become completely flaccid. It was the opinion of Hopkinson and Lightwood that progressively smaller diameter plugs could be used as the tone of the external sphincter muscle improved, and only occasional electrostimulation would be required to maintain continency.

Glen also found the intra-anal electrode plug to be an effective form of physiotherapy resulting in improved muscular tone. [J Pediatr. Surg., pp. 138-142 (1971)]Once voluntary control of the external sphincter muscle was achieved using electrostimulation, treatment would be discontinued briefly to evaluate the subject's progress toward unaided or spontaneous continence. Stimulation was required for shorter periods of time and for less frequent intervals to maintain continency during a course of treatment. The period of continuous electrical stimulation required to achieve control in the tested subjects varied from a period of weeks to several months. Glen concluded by recommending that electrical stimulation be employed as an aid to pelvic tone training as a treatment for incontinent individuals.

Van Der Mosel U.S. Pat. No. 3,749,100, discloses an electrostimulation probe comprising a suppository body formed with a rounded bulbous head, a reduced neck, and a broadened hilt, which is adapted to be inserted into the anus of a patient suffering from incontinence. The rounded bulbous tip and reduced neck facilitate anal insertion and subsequent retention. The rounded neck is clasped by the rectal sphincter, and is provided with a pair of spaced electrical contacts which rests against the sphincter. The broadened hilt limits insertion of the suppository body, and has a substantially flat base so as to permit the patient to sit or lie down comfortably with the device inserted. A pair of electrical leads are connected to the contacts, which are energized by a square wave signal having an average value of zero Volts, a peak potential not greater than 10 Volts and preferably between 1 and 2 Volts, and in the frequency range from about 18 to about 20 Hertz. Such electrostimulation is claimed to cause tonic and physiological contraction of the sphincter muscle, with significant results in the control of incontinence.

Stiebel et al, U.S. Pat. 3,403,684, disclose an electrical stimulator for supplying electrical stimulating pulses to preselected areas of the body. The stimulator comprises an elongated body having a bulbous portion at one end and a generally flat portion at the other end. The two end portions are interconnected by a generally narrow rod-like portion. A plurality of electrodes are formed on the bulbous end. In a preferred embodiment, the electrodes are spaced apart circumferential rings. The flat portion may contain a source of electrical energy and means for controlling the output of the device. The bulbous end contains a pulse timing circuit for controlling pulses of energy from the source of electrical energy to the plurality of electrodes.

Schaudinischky et al, Med. & biol. Engng. Vol. 7, pp. 341-343 (1969), describe shape conforming electrodes formed from flexible and elastic materials. In one embodiment, an electrode comprises a balloon-type elastic base with electrodes attached to the external surface of the balloon.

Geronimi-Stocker, Swiss Patent 206,545, describes an apparatus which can be inserted into the rectum of a patient. The apparatus comprises two electrodes. One electrode is adapted to contact the skin of the patient, and the other electrode is adapted to contact an organ to be treated.

Erlandsson, U.S. Pat. No. 4,106,511, describes an electrical stimulator for controlling the bladder and/or the rectal function. The stimulator comprises an expandable obdurator which is worn within the body. The obdurator is provided with electrodes which transmit a biphasic, pulsatile signal to the user.

Du Vall et al., U.S. Pat. No. 3,933,147, disclose an apparatus for treating disorders in the region of the pubococcygeous muscle. The apparatus comprises a probe having annular electrodes on the surface thereof. A pulsatile electrical signal is applied to the probe to stimulate the muscle.

Many of the devices described above are plug-like devices which operate by contracting the anal canal in the direction of its length, thereby closing the canal about the plug. It is an object of the present invention to provide a device which causes a contraction of the sphincter ani externus which closes the anal canal circumferentially.

Many of the prior art devices described above suffer from the disadvantage that once used, they must be cleaned before reinsertion. Additionally, in the case of rectal electrodes used to control incontinence, the electrodes must be removed and reinserted to permit defecation and reestablish continence, respectively. Continual removal and reinsertion can eventually lead to a physical deterioration of the electrode. Accordingly, it is an object of the present invention to provide a device for electrically stimulating the sphincter ani externus, which device utilizes an inexpensive, disposable electrode assembly which can be placed by a user over an anal probe body and easily removed therefrom, thereby eliminating the need to disinfect the electrodes between use, as well as the need to replace the entire device upon wear of the electrodes.

It is also an object of the present invention to provide a system for use in rehabilitating or training the sphincter ani externus, which system utilizes an electrical signal particularly adapted to aid in the restoration of voluntary control to this muscle. The system is adapted to contract the sphincter muscle by stimulating the muscle directly and by stimulating an afferent nerve which, by a spinal reflex, causes contraction of the muscle. The system is also adapted to stimulate a sensory nerve which enables the user to have a sensation and mental awareness of contraction.

SUMMARY OF THE INVENTION

These objects and others, which will be apparent from the description which follows, are realized in the present invention which provides a device for rehabilitation or training the sphincter ani externus. In its first embodiment, the present invention comprises a dimensionally stable body member adapted for insertion into the anus of a user. A flexible sleeve is provided to fit snugly over the main body member. The sleeve can be made from a dielectric, elastomeric material. Affixed to the external surface of the sleeve member are at least two, but preferably four circumferentially spaced-apart, longitudinal electrodes which are adapted to contact the external sphincter muscle.

Advantageously, the body member is provided with an electrical connector to receive electrical signals adapted for optimal stimulation of the sphincter muscle. The signal is communicated to the external electrodes on the sleeve through internal wiring in the main body member. The electrodes are made from a relatively nonabrasive, pliable nylon fabric containing chemically bonded silver. The sleeve can be removed from the main body member after use and discarded. At the next therapeutic session, a fresh, clean sleeve can be placed on the main body member and the device reinserted. Hence, problems of wear and contamination are reduced.

In its second embodiment, the present invention comprises a dimensionally stable body member adapted for insertion into the anus of a user. Affixed directly to the surface of the body member are at least two, but preferably four circumferentially spaced-apart, longitudinal electrodes which are adapted to contact the external sphincter muscle. Advantageously, the body member is provided with an electrical connector to receive electrical signals adapted for optimal stimulation of the sphincter muscle.

In both embodiments of the present invention, each of the spaced-apart, longitudinal electrodes has a predetermined surface area adapted to provide optimal stimulation of the sphincter muscle and to ensure that electrical energy is applied over a large enough surface area that localized tissue damage does not occur as an adverse side-effect.

Each embodiment of the present invention is adapted for use with signal generating means for producing a periodic output comprising a series of pulses of increasing peak voltage (from about zero volts to an adjustable maximum), followed by an off-period. Such an output is believed to provide for optimal rehabilitation of the sphincter ani externus.

BRIEF DESCRIPTION OF THE DRAWINGS

FIG. 1 is a side-elevational view of a sleeve member in accordance with the first embodiment of the present FIG. 2 is a side-elevational view of the sleeve of FIG. 1 rotated by 90 degrees.

FIG. 5 shows a side-elevational, partially cut away view of a two electrode apparatus in accordance with the second embodiment of the present invention.

FIG. 6 shows a cross-sectional view through line 6—6 in FIG. 5.

DETAILED DESCRIPTION OF THE INVENTION

Figure 3:
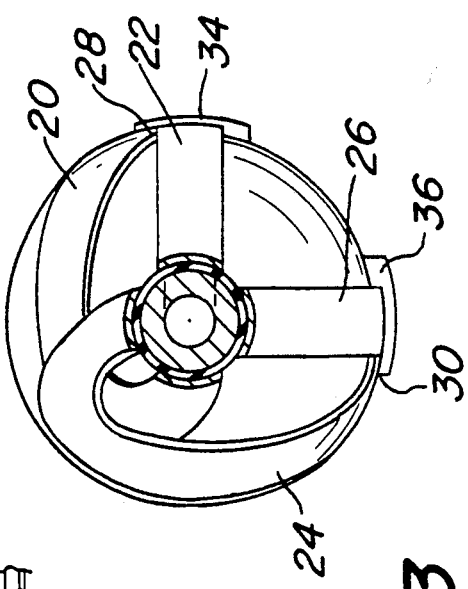
FIG. 3 is a cross-sectional view taken along line 3—3 of FIG. 2.

Referring now to the drawings, wherein like reference numerals indicate like elements, there is seen in FIGS. 1 and 2 a sleeve member 10 for use with one embodiment of the present invention.

The sleeve member 10 is made from a flexible, elastomeric, dielectric material such as latex. The sleeve member 10 comprises a tip portion 12, a mid-portion 14 and a base-portion 16. In a preferred embodiment, the sleeve member 10 may have a tab-pull 18 which can be used to manipulate the sleeve member 10.

Disposed on the outer surface of sleeve member 10 are four spaced-apart strip-like electrodes, 20, 22, 24 and 26, which are disposed along the length of the sleeve member 10, i.e., longitudinally.

Referring to FIG. 1, it can be seen that electrodes 22 and 20 are electrically connected to each other at an electrical connection point 28 within the base-portion 16 of sleeve member 10. The electrode 22 is disposed in a straight line from the electrical connection point 28 to a point just below the tip portion 12. The electrode 20 is curved within the base-portion 16 to the mid portion 14 where electrode 20 is then disposed in a straight line to a point just below the tip portion 12.

Referring to FIG. 2, it can be seen that electrode 22 is disposed in a straight line from electrical connection point 28 to just below the tip portion 12. Electrode 20 is curved within base-portion 16. Hence, it will be appreciated that electrodes 20 and 22 are spaced apart from each other within mid-portion 14 by 180 degrees. It will also be appreciated that electrodes 20 and 22 are electrically connected to each other.

Again referring to FIGS. 1 and 2, it can be seen that there are two additional spaced-apart, electrically connected electrodes 24 and 26. Like electrodes 20 and 22, electrodes 24 and 26 both emanate from an electrical connection point 30 within the base-portion 16 of sleeve member 10. Referring to FIG. 2, it can be seen that electrode 26 lies in a straight line from electrical connection point 30 to just below tip-portion 12. Referring to FIG. 1, it can be seen that electrode 24 is curved within the base-portion 16, but lies in a straight line in mid-portion 14 of sleeve member 10. It will also be appreciated that electrodes 24 and 26 are electrically connected to each other.

The arrangement of all four electrodes 20, 22, 24 and 26 on the sleeve member 10 perhaps can be seen best with reference to FIG. 3 which is a cross-sectional view of the sleeve member of FIG. 2 taken along line 3—3. It can be seen that electrodes 20 and 22 emanate from electrical connection 28. Electrode 20 is curved in base-portion 16 so that it is disposed on mid-portion 14 180 degrees opposite electrode 22, which is disposed in a straight line from electrical connection point 28. Similarly, electrode 24 is curved in base-portion 16 so that it is disposed 180 degrees opposite electrode 26, which is disposed in a straight line from electrical connection point 30.

The electrodes 20, 22, 24 and 26 are preferably thin strips of an electrically conductive cloth such as Swift Textile #SN 300-7224 which comprises nylon containing chemically bonded silver. The electrodes 20, 22, 24 and 26 can be attached to sleeve member 10 using a biocompatible substrate adhesive such as 3M #1512. A rubber adhesive can be used in drops 32, 32' to secure the end portions of the electrodes 20, 22, 24 and 26 to the sleeve member 12.

Referring again to FIG. 3, it can be seen that electrodes 20 and 24 cross over one another. To prevent electrodes 20 and 24 from short-circuiting, the electrodes 20 and 24 can be coated in their cross-over regions which dielectric film such as the material sold under the trademark Tegaderm ®, which is a transparent dressing sold by 3M Medical Products Division (1628NS).

To facilitate the connection of the sleeve member 10 to the body member of the apparatus (described below), the electrical connection points 28 and 30 can be in electrical communication with electrical connectors 34 and 36. Preferred connectors are metal snaps such as those used in garments. Either the male or female snap may be used, it being understood that if the male snap is used on the sleeve member 10, the Each of the electrodes 20, 22, 24 and 26 must have a surface area large enough to avoid causing tissue injury as a result of the application of electrical energy to the tissue.

Figure 4:
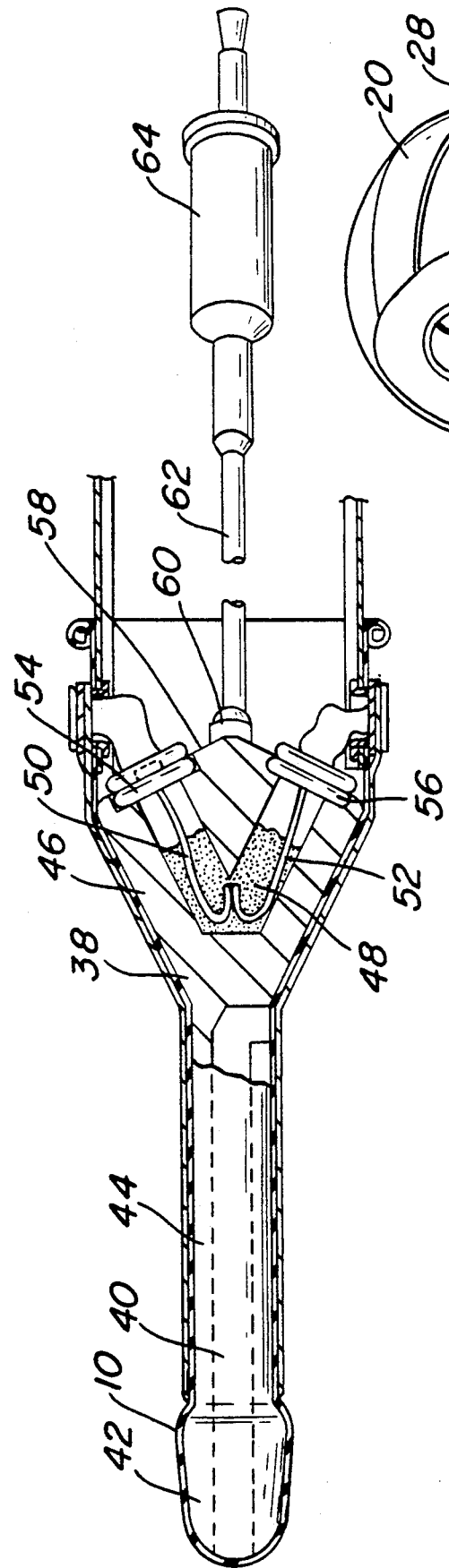
FIG. 4 is a cross-sectional view of the apparatus in accordance with the first embodiment of the present invention, showing both the sleeve member and the body member.

Referring now to FIG. 4, there can be seen in cross-section the entire apparatus of the first embodiment of the present invention. The apparatus comprises the sleeve member 10 and a body member 38 shown in cross-section. The body member must be dimensionally stable so that flexible sleeve member 10 may be fit snugly thereover. Suitable materials for the body member include acrylonitrile butydine styrene LEXAN ®, PERSPEX ®, and methyl methacrylate, the latter being preferred. To facilitate placing sleeve member 10 over body member 38, an air vent 40 may be provided in body member 38. Hence, as sleeve member 10 is fit over body member 38, entrapped air is forced out though vent 40. The body member 38, like the sleeve member 10, comprises a tip portion 42, a reduced neck 40, and a broadened base-portion 46. The tip portion 12, mid-portion 14 and base-portion 16 of sleeve member 10 are adapted to lie over tip-portion 42, reduced neck 40 and broadened base 46, respectively, of body member 38.

Within the broadened base 46 is a channel 48. The channel 48 contains wires 50 and 52 which are connected at one end to male or female snap members 54 and 56 which are adapted to engage electrical connectors 34 and 36 of sleeve-member 10. Snap members 54 and 56 are disposed on the outer surface 58 of the broadened-base 38. The other ends of wires 50 and 52 are connected (not shown) to a jack (not shown) on broadened base 38. The jack (not shown) is adapted to receive a plug 60 which is connected to a cable 62, which, in turn, is connected to a second plug 64 which is adapted to connect with electronics adapted to drive the apparatus.

As is shown in FIG. 4, the apparatus of the present invention broadly comprises a rigid base member fitted with a disposable, flexible sleeve member having four spaced-apart longitudinal electrodes, the four electrodes being grouped into two pairs. Each member of a pair is disposed 180 degrees from the other member. Furthermore, each member of a pair is electrically connected to the other member of the pair. The apparatus is adapted to be removably wired to external electronics.

The second embodiment of the invention is shown in FIGS. 5, 6, 7 and 8. The apparatus in accordance with the present invention is indicated generally by the reference numeral 70.

Referring now to FIG. 5, the apparatus 70 comprises a dimensionally stable body member 72 which comprises a tip portion 74, a reduced neck portion 76, and a broadened base portion 78. The body member may be made of any biocompatible material, including acrylonitrile butydine styrene, methyl methacrylate, and polyvinyl chloride, the latter being preferred. Disposed on the outer surface of the neck portion 76 are two electrodes 78, 80. The electrodes run longitudinally along the length of the neck portion 76. The electrodes 78, 80 are made of any biocompatible metal. The surface area of the electrodes is chosen for optimal stimulation, without tissue injury.

Advantageously, the forward-most portion of the electrodes 78, 80, indicated generally by reference numeral 82 is embedded within the tip portion 74 so that the edge of the portion 82 does not peel away from the surface of the body member 72 as a result of repeated insertion and removal. The electrodes 78, 80 can be attached to the surface of the body member 72 using a biocompatible adhesive such as silicone rubber. Such an adhesive also prevents contaminants from becoming embedded between the electrodes 78, 80 and the surface of the body member 72.

In a preferred embodiment, the electrodes 78, 80 are recessed slightly into the body member 72.

The base 78 contains an interior chamber 84. The base 78 is provided with a port 86 which communicates with the interior chamber 84.

Disposed within the port 86 is a strain-relief member 88. One end of a wire 90 is directed into the chamber 84 through strain-relief member 88. The wire can be connected to electrodes 78 and 80 (whose rearward ends are disposed within the chamber) by any suitable means, including soldering or by crimp terminals, as indicated by reference numeral 92, 92'.

The other end of the wire 90 can be fitted with a plug 94 adapted for insertion into external electronics (not shown).

Referring now with reference to FIG. 6, it can be seen that the electrodes 78, 80 are spaced apart from each other, and slightly recessed into the surface of body member 72.

Figure 7:
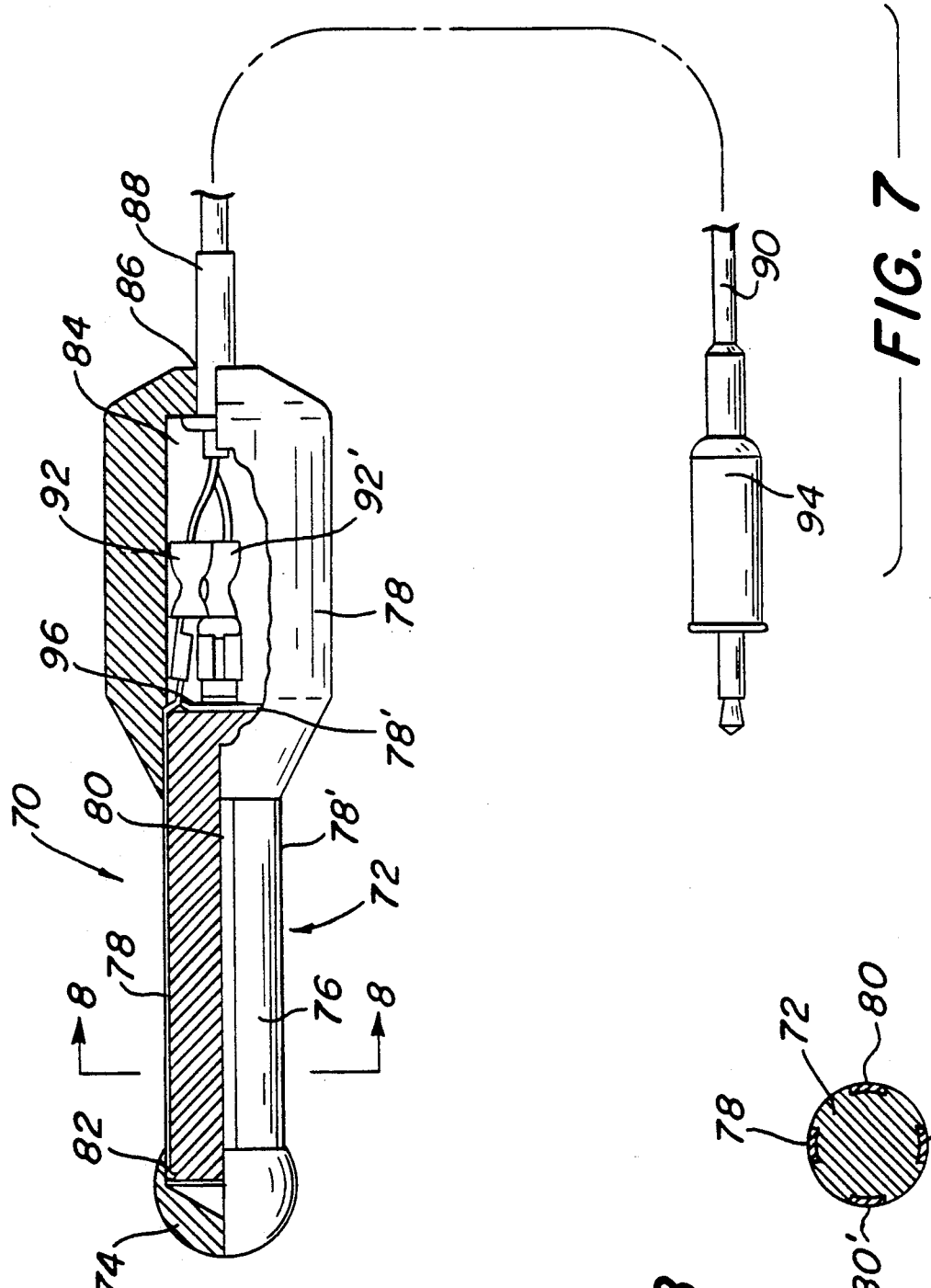
FIG. 7 shows a side-elevational, partially cut-away view of a four electrode apparatus in accordance with the second embodiment of the present invention.
Figure 8:
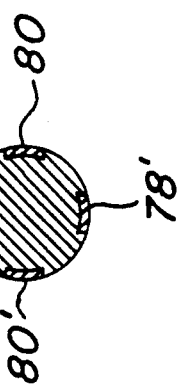
FIG. 8 shows a cross-sectional view through line 8—8 in FIG. 7.

The most preferred embodiment of apparatus 70 is shown in FIGS. 7 and 8. In this most preferred embodiment, the apparatus 70 comprises two pairs of electrically connected electrodes. As can be seen best in FIG. 8, the four electrodes are evenly circumferentially spaced-apart on the neck portion 72 of the apparatus. As can be seen best in FIG. 7, the two electrodes 78, 78' which are spaced about 180 degrees apart from each other are electrically connected at an electrical connection point 96 in the chamber 84 in the base portion 78 of the body member 72.

Similarly, the electrodes 80, 80' are spaced apart from each other by about 180 degrees and electrically connected in the base portion 78 of the body member 72.

In the preferred embodiment, the electrical connections are made using crimp terminals 92, 92'.

Figure 10:
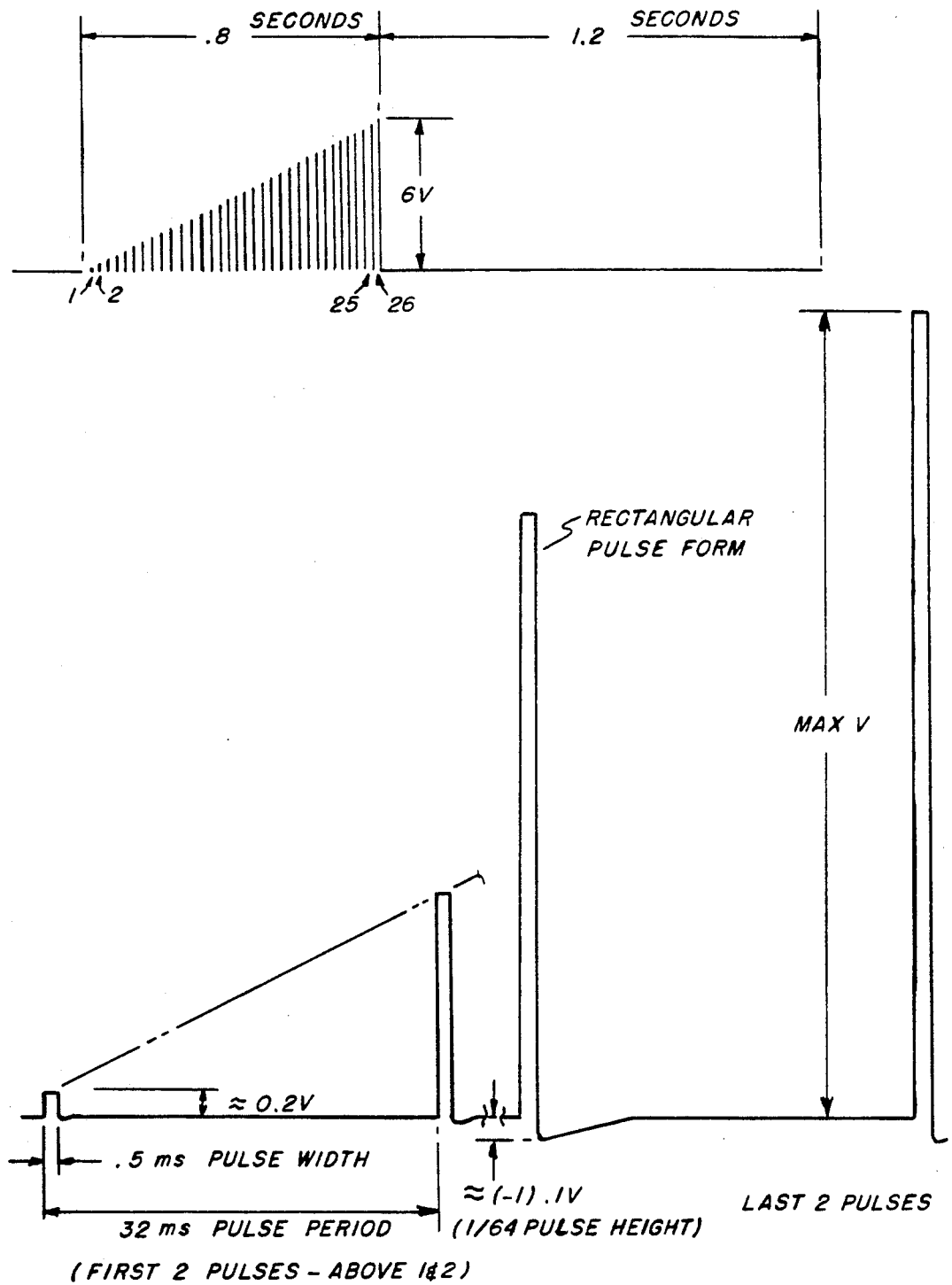
FIG. 10 shows the preferred electrical signal for use with both embodiments of the present invention.

The external electronics of the present invention should produce a periodic, biphasic pulsatile waveform. The pulses should increase linearly from 0 V to an adjustable maximum, generally in the range of 2 to 10 V. A preferred waveform is shown in FIG. 10. The waveform comprises a series of 26 pulses whose peak voltage increases linearly from 0 V to the maximum. Each pulse has a duration of 0.5 milliseconds. The pulses are separated from each other by 32 milliseconds. Each pulse train has a duration of 0.8 seconds and is followed by a an off-period of 1.2 seconds. As can be seen in FIG. 10, each pulse undershoots, the 0 V axis and gradually rises back to 0 V. The area of the undershoot following each pulse should equal the area of the positive pulse itself. In this way, there is no net DC voltage.

Figure 9A:
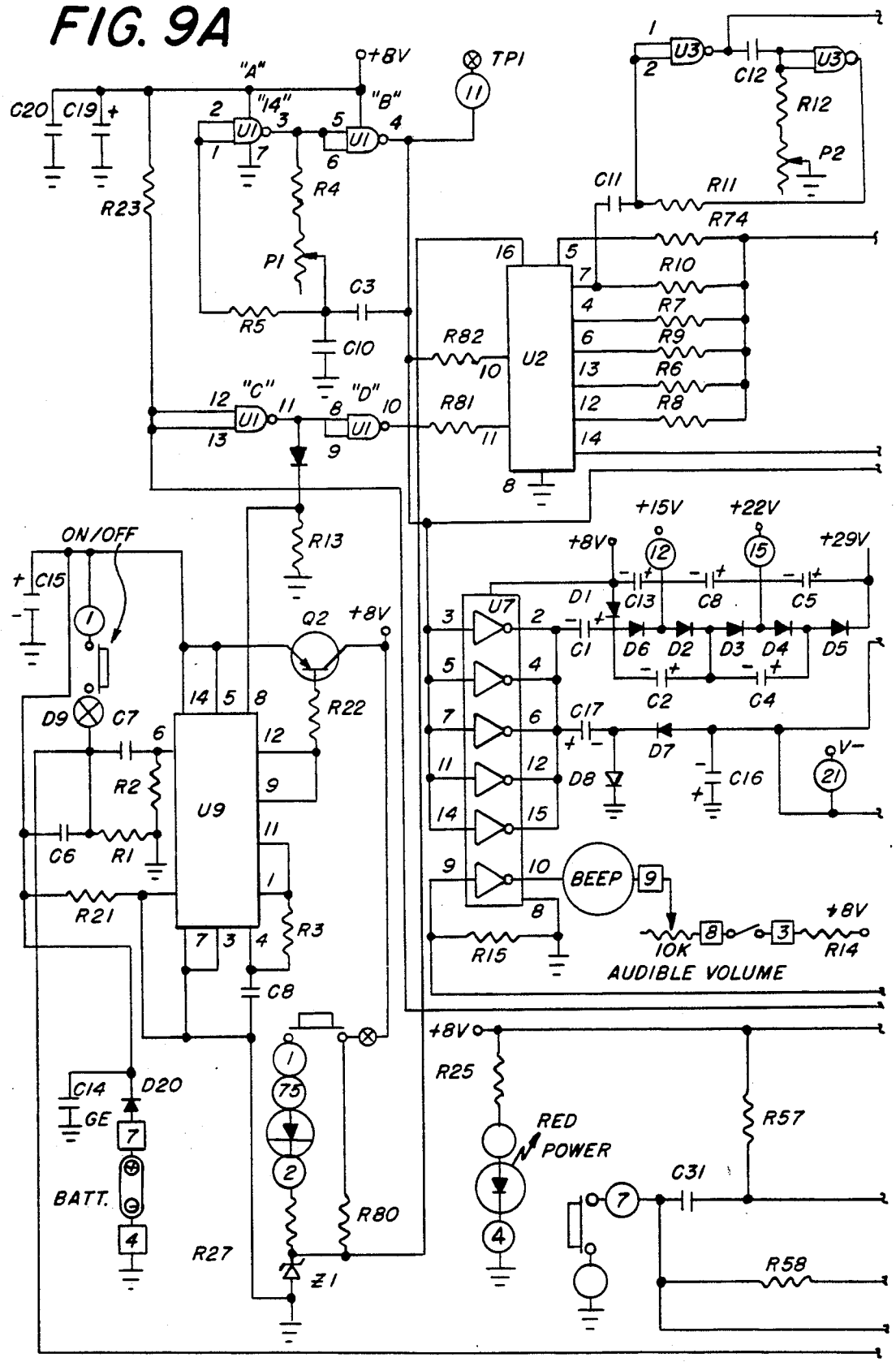
FIGS. 9A, 9B and 9C show an electronic circuit for use with both embodiments of the present invention.
Figure 9B:
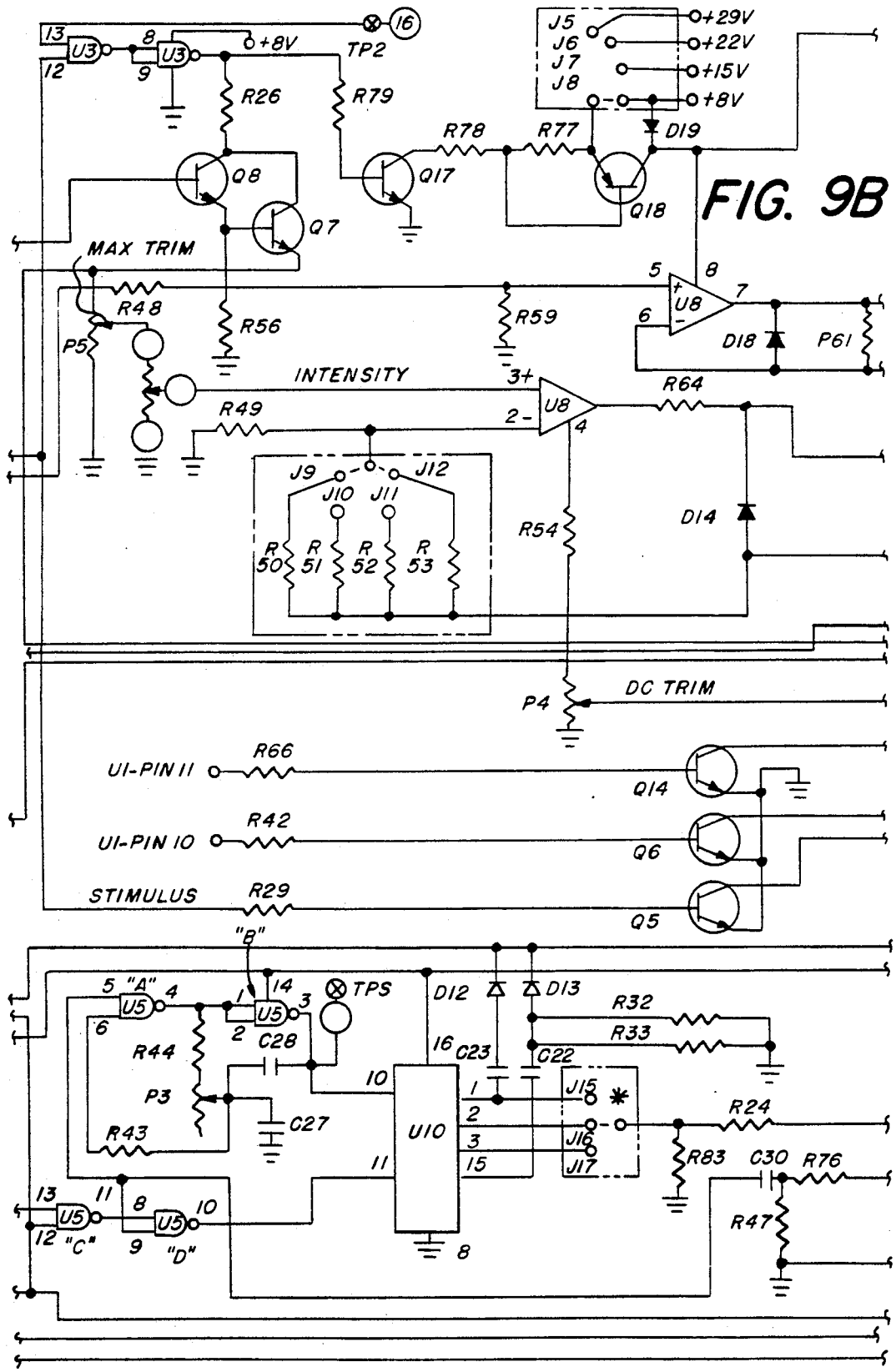
Figure 9C:
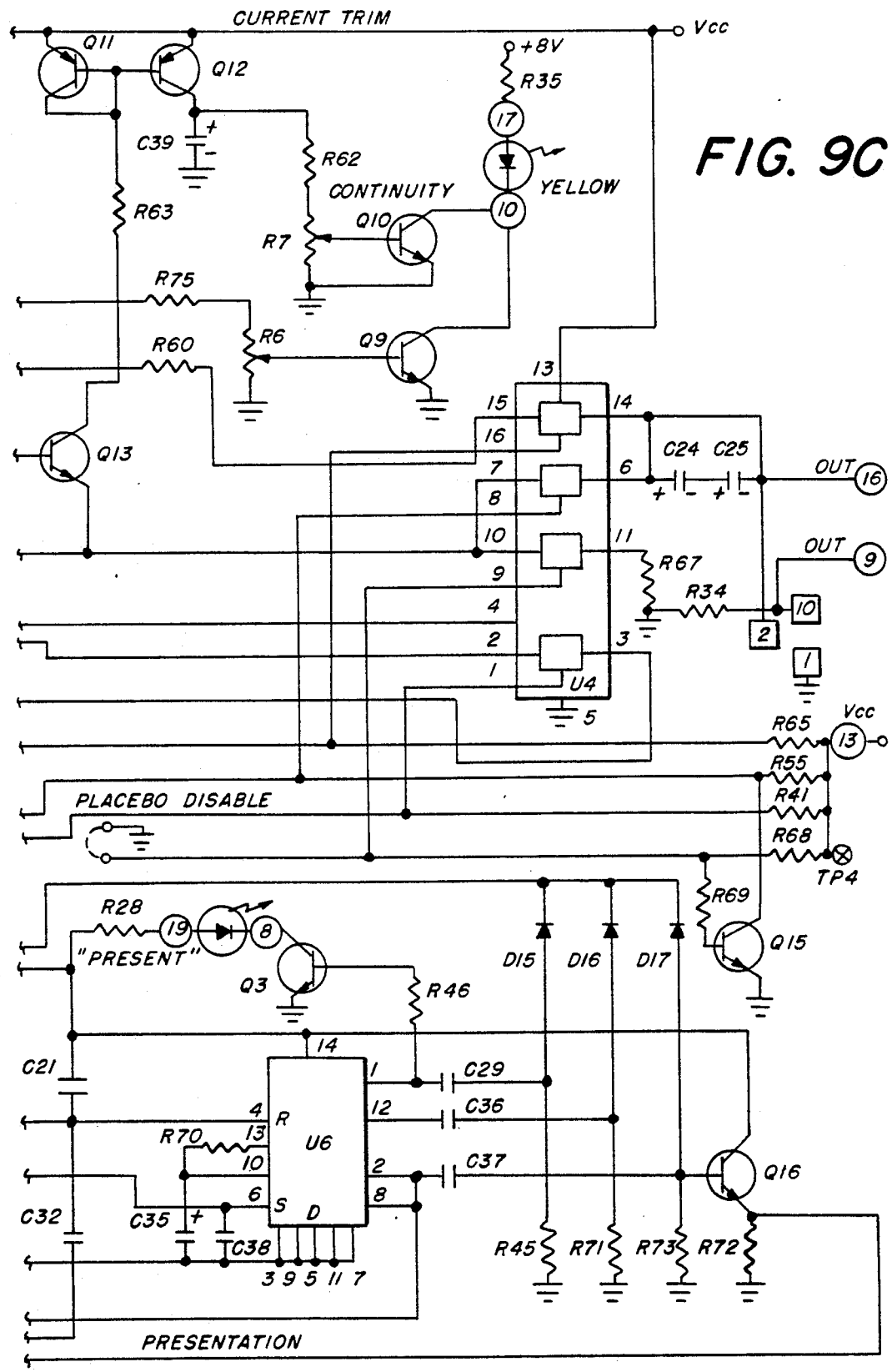

A preferred circuit for producing the desired signal is shown in FIGS. 9A, 9B and 9C. Values of analog components are specified in the table below.

| VALUES FOR ANALOG COMPONENTS (all capacitors in microfarads, all resistors in ohms) | |
|---|---|
| C1 | .01 |
| C2 | 22 |
| C3 | 22 |
| C4 | |
| C5 | 22 |
| C6 | .001 |
| C7 | .01 |
| C8 | .01 |
| C9 | .01 |
| C10 | .001 |
| C11 | .01 |
| C12 | .01 |
| C13 | 22 |
| C15 | 220 |
| C16 | 10 |
| C17 | 2.2 |
| C19 | 220 |
| C20 | .05 |
| C21 | .05 |
| C22 | .047 |
| C23 | .047 |
| C24 | 10 |
| C25 | 10 |
| C26 | |
| C27 | .001 |
| C28 | .22 |
| C29 | .047 |
| C30 | .01 |
| C31 | .01 |
| C32 | .01 |
| C35 | 2.2 |
| C36 | .047 |
| C37 | .047 |
| C38 | .001 |
| C39 | 1.0 |
| Q1 | 2N3906 |
| Q2 | 2N3906 |
| Q3 | 2N3904 |
| Q4 | 2N3904 |
| Q5 | 2N3904 |
| Q6 | 2N3904 |
| Q7 | 2N3904 |
| Q8 | 2N3904 |
| Q9 | 2N3904 |
| Q10 | 2N3904 |
| Q11 | 2N3906 |
| Q12 | 2N3906 |
| Q13 | 2N3904 |
| Q14 | 2N3904 |
| Q15 | 2N3904 |
| Q16 | 2N3904 |
| Q17 | 2N3904 |
| Q18 | 2N3906 |
| R1 | 100k |
| R2 | 100k |
| R3 | 1M |
| R4 | 68k |
| R5 | 2.2M |
| R6 | 49.9k |
| R7 | 220k |
| R8 | 24.9k |
| R9 | 100k |
| R10 | 1M |
| R11 | 33k |
| R12 | 22k |
| R13 | 100k |
| R14 | 150 |
| R15 | 10M |
| R21 | 10M |
| R22 | 10k |
| R24 | 1M |
| R25 | 4.7k |
| R26 | 10 |
| R27 | 150 |
| R28 | 1k |
| R29 | 10M |
| R32 | 10M |
| R33 | 10M |
| R34 | 10M |
| R35 | 1k |

-continued

| VALUES FOR ANALOG COMPONENTS (all capacitors in microfarads, all resistors in ohms) | |
|---|---|
| R41 | 1M |
| R42 | 10M |
| R43 | 2.2M |
| R44 | 68k |
| R45 | 10M |
| R46 | 10k |
| R47 | 10K |
| R48 | 100k |
| R49 | 1M |
| R50 | 560k |
| R51 | 2.2M |
| R52 | 3.9M |
| R53 | 5.6M |
| R54 | 100k |
| R55 | 1M |
| R56 | 10k |
| R57 | 1M |
| R58 | 1M |
| R59 | 1k |
| R60 | 1k |
| R61 | 470k |
| R62 | 10k |
| R63 | 150 |
| R64 | 3.3k |
| R65 | 1M |
| R66 | 10M |
| R67 | 2.2k |
| R68 | 1M |
| R69 | 10M |
| R70 | 330k |
| R71 | 10M |
| R72 | 100k |
| R73 | 10M |
| R74 | 470k |
| R75 | 100k |
| R76 | 1k |
| R77 | 470k |
| R78 | 10k |
| R79 | 47k |
| R80 | 10k |
| R81 | 100k |
| R82 | 100k |
| R83 | 1M |
| P1 | 100k |
| P2 | 100k |
| P3 | 100k |
| P4 | 10k |
| P5 | 10k |
| P6 | 1M |
| P7 | 1M |
| Z1 | IN5232B |

This circuit is comprised of both analog and digital circuit elements arranged to perform several principal functions. These are power control, waveform generation, dosage timing, dose counting and output control and monitoring. There are also several status indicator light emitting diodes and an audible tone annunciator.

POWER CONTROL

The power control portion of the circuit comprises a dual "D" flip-flop U9 (RCA CD 4013B) for example), an on/off switch and a series pass transistor Q2. Flip-flop #1 of U9 generates a 5 msec positive pulse at its Q (pin #1) output each time the on/off switch is pressed and serves to "de-bounce" the on/off switch signal. This pulse is used as the clock pulse for flip-flop #2 which is connected so as to "toggle" on-off for every clock pulse. When the on/off switch is depressed, a positive pulse is momentarily coupled through C7 to the "set" input of flip-flop #1 of U9 causing the "Q1" output (pin #1) to go positive. Capacitor C8, connected to the "reset" input of flip-flop #1, charges through R3 toward the positive pin #1 potential. When the reset switching threshold is exceeded, flip-flop #1 resumes its original state with Q1 off, i.e., at ground. The 5 millisecond positive pulse thus generated by flip-flop #1 by depressing the on/off switch serves as the clock input to flip-flop #2 which is connected to "toggle", i.e. change from Q2HI, Q2LO to the opposite state, Q2LO, Q2HI, or vice versa, each time a clock pulse positive transition occurs at pin 11 (flip-flop #2 clock input) - provided neither its set nor reset (pins 8 and 10, respectively) are not HI (which is so except during an active "stimulus present" 3 minute cycle). The Q2 (pin 12) output from U9 controls the base voltage of series pass NPN transistor Q2, thus applying or removing the battery supply to the remainder of the circuits. The circuits of U9 always have voltage applied. The circuits are arranged, however, to draw no current quiescently.

After the on/off switch, U9 and Q2 have turned on the device, the "power" LED turns on and the stimulus waveform generator "clock", i.e., the astable multivibrator (formed by U1A, U1B, C9, R4, R5 and P1) starts. The 2 millisecond period clock signal generated by the clock is applied to the "staircase" generator counter U2 (an RCA CD4020 for example) and to voltage multiplier driver U7, (a CD4049 hex inverter). In conjunction with diodes D1, D2, D3, D4, D5, D6, D7 & D8 and capacitors C1, C2, C3, C4, C5, C13, C16 & C17, U7 generates a variety of DC supply voltages, namely nominal −8, +15, +22 and +29 volts for later use in the generator output stage as a selectable power source and signal range (jumpers J5 through J12). Jumpers J5 and J10 are preferred. Five of the six inverters are used in parallel to provide adequate multiplier drive power. The sixth inverter is used as a driver for a piezo audible annunciator.

DOSE TIMER

When the power control circuits are activated, as described above, power is applied to all the remaining circuitry, but no signal output occurs until the dose timer portion of the circuit [comprised of gates U5 (CD4011), counter u U10 (CD4020) and dual "D" flip-flop U6 (CD4013)]is activated by momentarily depressing the "stimulus present" switch. Flip-flop U6 was forced to come on with pin 1 (Q1) in the low state at power up as arranged by having capacitor C21 couple a positive pulse to the U6 flip-flop #1 reset input pin 4 at that time. Pressing the "Stim Present" switch couples a negative pulse to the U5A inverting gate, which in turn applies a positive pulse through C30 to the U6, flip-flop #1 "Set" input (pin 6) and lights the "stim present" LED through Q3. Output Q1 (pin 2) of U6 is connected through inverter U5C and U5D to the reset (pin 11) of counter U10, the dose timer, and also through inverters U1C and U1D to the reset (pin 11) of staircase generator counter U2 (CD4020). These counters, which were brought on with their resets held high by U6 pin 2, and the dose timer astable multivibrator comprised of U5, U5A, U5B, C28, R43, P3, which was disabled by an inverted Q1 through U5A, are now free to operate. To recapitulate, pressing the "Stim Present" switch lights the stim present LED and starts the dose timer which enables the waveform generator and thus the source of output signal. This enablement continues while dose counter U10 counts the astable multivibrator output pulses until a count of $2^{13}$ causes U10 pin 2 to go positive. This is coupled through R24 to the reset input (pin 4) of dose timer flip-flop U6 turning pin 1 off and pin 2 on, which again disables counters U10 and U6. The dose timer output is also coupled back to the stim present switch and to the power control flip-flop U9 to prevent turning off the unit in the midst of a dose administration.

Dose timer counter U10 and flip-flop U6 supply positive pulse signals via C22, C23, C29, C36 & C37 to the piezo annunciator driver section of U7 such that audible beeps are generated at 45 second intervals during the dose time and a double beep is given at the conclusion of the interval. The second flip-flop of U6 is connected so as to provide the second beep after flip-flop #1 has turned off.

The time of the dose interval is determined by the choice of jumpers J15, J16 or J17 and the adjustment of P3 in the astable multivibrator circuit. The usual adjustment of P3 gives a choice of 1 ½, 3 and 6 minutes dose time for the three jumper positions.

WAVEFORM GENERATOR

The stimulating waveform generator is powered from a zener diode (to maintain constant output over battery life) and consists of (1) counter U2 (CD4020), (2) binarily related resistors R6, R7, R8, R9, R10 and R74 which generate a linearly rising staircase signal at the base of Q8, and (3) the pulsing circuit comprised of U3, R11, R12, C11, C12 and P2 which gate "on" the collectors of Q8 and Q7 for only 0.5 milliseconds at each staircase step. Q8 an Q7 are therefore turned off except during the pulse time. In addition to the pulsed gating of the staircase signal, it is also gated on and off by the counter output pin 14 to provide 0.8 second on-period followed by a 1.2 second off-period. The gated train of increasing amplitude pulses at the emitter of Q7 is coupled through the "MAXTRIM" and "Intensity" potentiometers to output Op Amp U8 (LM 358) and transistor Q13 and then to the output terminal through analog switch U4 (preferably, U4 is replaced with a short circuit from pin 6 to 7) and coupling capacitors C24 and C25 to the device output terminals.

OUTPUT MONITORING

The output circuit consists of emitter follower Q13 driven by Op Amp U8. The current supplied to the load comes from the Q13 emitter. The collector current is substantially equal to the emitter current and is used to monitor load current via current mirror Q11, Q12 and transistor Q10 which drives a "Continuity" LED. The LED pulses on in response to load current supplied by the generator. Any open wire in the connecting cable or apparatus will be indicated by no continuity LED Light when the intensity control is advanced during stimulus presentation.

The apparatus in accordance with the present invention is used as follows:

A physician first evaluates the eligibility of a patient for treatment with the apparatus electrically by stimulating the external sphincter muscle of the patient with a glove-like device whose finger contains surface electrodes such as those used on the apparatus (described in U.S. Ser. No. 696,048, filed Jan. 29, 1985). If the patient's muscle is physiologically capable of responding to the stimulus, the physician will feel a tightening of the muscle about his finger.

Next, the apparatus in accordance with the invention is lubricated with a suitable lubricant, such as Parker 360 electrode gel, and inserted into the anus of the patient. The electronics is turned on, and the maximum amplitude of the pulsatile output is gradually increased until the patient senses a contraction of the sphincter muscle. The amplitude is increased even further until the patient just begins to experience some discomfort, and is then decreased to just below the discomfort threshold. The treatment is continued for a total of about three minutes. After a suitable relaxation period, during which no stimulation is applied, generally on the order of one to several minutes, the three-minute stimulation session is repeated.

It has been found that optimum training of the sphincter muscle can be achieved if stimulation, as described above, is applied in three daily cycles, each cycle containing three three-minute sessions, each session being separated from the other sessions by one to several minutes, and each cycle being separated from the other cycles by one to several hours. In general, the first cycle is administered by a physician; subsequent cycles are administered by the patient at his convenience.

It will be understood that the foregoing description is offered by way of illustration, and that the present invention is defined with reference to the claims which follow.

What is claimed is:

1. Apparatus for use in training the sphincter ani externus of a patient, comprising, a body member comprising a tip portion, a reduced neck joined at one end thereof to said tip portion, and a broadened base joined to said reduced neck at the other end thereof;

a sleeve member comprising a tip portion, a mid portion and a base portion, said sleeve being adapted to fit snugly over and conform to said body member, said sleeve member being made from a flexible, elastomeric dielectric material, said sleeve member comprising four circumferentially spaced-apart electrodes extending longitudinally along at least a portion of the outer surface of said mid portion of said sleeve member and adapted to contact the sphincter ani externus of the patient.

2. The apparatus of claim 1 wherein said four electrodes are grouped into two pairs, each pair comprising two electrodes spaced about 180 degrees apart from each other, said two electrodes being electrically connected to each other, but not electrically connected to the other pair.

3. The apparatus of claim 2 wherein the electrodes of each pair of electrically connected at an electrical connection point at the base portion of said sleeve.

4. The apparatus of claim 3 wherein said electrical connection point is in electrical communication with an electrical connector at the base portion of said sleeve.

5. The apparatus of claim 4 wherein said electrical connector is affixed to said sleeve.

6. The apparatus of claim 1 wherein said body member comprises electrical connectors at the base thereof, which connectors are adapted to connect with and make electrical contact with said electrical connectors of said sleeve when said sleeve is fitted over said body member.

7. The apparatus of claim 1 wherein said electrodes comprise a fabric of conductive threads.

8. The apparatus of claim 7 wherein said fabric comprises nylon containing chemically bonded silver.

9. The apparatus of claim 1 wherein the elastomeric dielectric material is latex.

* * * * *